United States Patent
Freeman et al.

(10) Patent No.: US 9,682,162 B2
(45) Date of Patent: Jun. 20, 2017

(54) STERILIZATION METHODS FOR MEDICAL DEVICES

(71) Applicant: Abbott Cardiovascular Systems Inc., Santa Clara, CA (US)

(72) Inventors: Abigail Freeman, Del Mar, CA (US); Bin Huang, Pleasanton, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 483 days.

(21) Appl. No.: 14/153,477

(22) Filed: Jan. 13, 2014

(65) Prior Publication Data

US 2014/0123602 A1 May 8, 2014

Related U.S. Application Data

(62) Division of application No. 11/893,230, filed on Aug. 14, 2007, now Pat. No. 8,747,738.

(60) Provisional application No. 60/838,030, filed on Aug. 15, 2006.

(51) Int. Cl.
| | |
|---|---|
| *A61L 2/18* | (2006.01) |
| *A61L 2/07* | (2006.01) |
| *A61L 2/08* | (2006.01) |
| *A61L 2/20* | (2006.01) |
| *A61L 2/22* | (2006.01) |
| *A61F 2/00* | (2006.01) |
| *A61F 2/82* | (2013.01) |

(Continued)

(52) U.S. Cl.
CPC *A61L 2/18* (2013.01); *A61L 2/07* (2013.01); *A61L 2/08* (2013.01); *A61L 2/081* (2013.01); *A61L 2/082* (2013.01); *A61L 2/085* (2013.01); *A61L 2/087* (2013.01); *A61L 2/186* (2013.01); *A61L 2/208* (2013.01); *A61L 2/22* (2013.01); *A61F 2/0095* (2013.01); *A61F 2/82* (2013.01); *A61F 2/86* (2013.01); *A61F 2/91* (2013.01); *A61L 2202/23* (2013.01); *A61L 2202/24* (2013.01); *A61L 2420/02* (2013.01)

(58) Field of Classification Search
CPC . A61L 2/08; A61L 2/081; A61L 2/082; A61L 2/087; A61L 2420/02; A61L 2202/24
See application file for complete search history.

(56) References Cited

U.S. PATENT DOCUMENTS

| | | | |
|---|---|---|---|
| 4,801,427 | A | 1/1989 | Jacob |
| 4,813,210 | A | 3/1989 | Masuda et al. |
| 4,818,488 | A | 4/1989 | Jacob |

(Continued)

FOREIGN PATENT DOCUMENTS

| | | |
|---|---|---|
| DE | 102 16 971 | 10/2003 |
| EP | 1 270 018 | 1/2003 |

(Continued)

OTHER PUBLICATIONS

U.S. Appl. No. 10/883,242, filed Jun. 30, 2004, Roorda et al.

(Continued)

*Primary Examiner* — Timothy Cleveland
(74) *Attorney, Agent, or Firm* — Squire Patton Boggs (US) LLP (57) ABSTRACT

Methods of sterilizing medical devices, including implantable medical devices like stents, chemically and with radiation are disclosed. Methods of preparing a sterile, packaged medical device, including a sterile, packaged implantable medical device or stent are disclosed.

10 Claims, 1 Drawing Sheet

(51) Int. Cl.
*A61F 2/86* (2013.01)
*A61F 2/91* (2013.01)

(56) References Cited

U.S. PATENT DOCUMENTS

| | | | |
|---|---|---|---|
| 4,898,715 A | 2/1990 | Jacob | |
| 4,909,995 A | 3/1990 | Jacob | |
| 4,917,586 A | 4/1990 | Jacob | |
| 4,931,261 A | 6/1990 | Jacob | |
| 4,943,417 A | 7/1990 | Jacob | |
| 4,997,625 A | 3/1991 | Simon et al. | |
| 5,041,287 A | 8/1991 | Driggers et al. | |
| 5,413,759 A | 5/1995 | Campbell et al. | |
| 5,413,760 A | 5/1995 | Campbell et al. | |
| 5,472,664 A | 12/1995 | Campbell et al. | |
| 5,480,302 A | 1/1996 | Fife | |
| 5,485,496 A | 1/1996 | Lee et al. | |
| 5,496,302 A | 3/1996 | Minshall et al. | |
| 5,573,732 A | 11/1996 | Waggener et al. | |
| 5,650,693 A | 7/1997 | Campbell et al. | |
| 5,660,873 A | 8/1997 | Nikolaychik et al. | |
| 5,730,933 A | 3/1998 | Peterson | |
| 5,787,144 A | 7/1998 | Findlay | |
| 5,837,313 A | 11/1998 | Ding et al. | |
| 6,106,454 A | 8/2000 | Berg et al. | |
| 6,149,864 A | 11/2000 | Dillow et al. | |
| 6,345,449 B1 | 2/2002 | Lepore | |
| 6,358,556 B1 | 3/2002 | Ding et al. | |
| 6,408,538 B1 | 6/2002 | Lepore | |
| 6,447,718 B1 | 9/2002 | Carter et al. | |
| 6,527,801 B1 | 3/2003 | Dutta | |
| 6,528,015 B1 | 3/2003 | Lin et al. | |
| 6,787,179 B2 | 9/2004 | Timm et al. | |
| 6,858,181 B2 | 2/2005 | Aoyagi | |
| 6,923,936 B2 | 8/2005 | Swanson et al. | |
| 6,933,026 B2 | 8/2005 | Mauze et al. | |
| 6,953,625 B2 | 10/2005 | Koulik | |
| 6,986,868 B2 | 1/2006 | Madsen | |
| 7,001,873 B2 | 2/2006 | McDonnell et al. | |
| 7,108,832 B2 | 9/2006 | Christensen et al. | |
| 7,150,853 B2 | 12/2006 | Lee et al. | |
| 7,179,419 B2 | 2/2007 | Lin et al. | |
| 7,959,857 B2 | 6/2011 | Freeman et al. | |
| 7,998,404 B2 | 8/2011 | Huang et al. | |
| 8,034,287 B2 | 10/2011 | Freeman et al. | |
| 8,246,904 B2 | 8/2012 | Freeman et al. | |
| 8,252,228 B1 | 8/2012 | Freeman et al. | |
| 8,298,483 B2 | 10/2012 | Freeman et al. | |
| 8,318,088 B2 | 11/2012 | Freeman et al. | |
| 8,461,561 B2 | 6/2013 | Freeman et al. | |
| 8,471,229 B2 | 6/2013 | Freeman et al. | |
| 8,524,151 B2 | 9/2013 | Freeman et al. | |
| 8,569,726 B2 | 10/2013 | Huang et al. | |
| 8,696,984 B2 | 4/2014 | Freeman et al. | |
| 8,709,340 B2 | 4/2014 | Freeman et al. | |
| 8,747,736 B2 | 6/2014 | Huang et al. | |
| 8,747,738 B2 | 6/2014 | Freeman | |
| 8,956,575 B2 | 2/2015 | Freeman et al. | |
| 9,155,806 B2 | 10/2015 | Freeman et al. | |
| 9,339,568 B2 | 5/2016 | Huang et al. | |
| 2002/0037943 A1 | 3/2002 | Madsen | |
| 2002/0051812 A1 | 5/2002 | DiCosmo et al. | |
| 2002/0071902 A1 | 6/2002 | Ding et al. | |
| 2003/0083616 A1 | 5/2003 | Lee et al. | |
| 2003/0136426 A1 | 7/2003 | Ayogai | |
| 2003/0175408 A1 | 9/2003 | Timm et al. | |
| 2004/0048016 A1 | 3/2004 | Wang et al. | |
| 2004/0157017 A1 | 8/2004 | Mauze et al. | |
| 2005/0013729 A1 | 1/2005 | Brown-Skrobot et al. | |
| 2005/0025667 A1 | 2/2005 | Christensen | |
| 2005/0060041 A1 | 3/2005 | Phan et al. | |
| 2005/0079096 A1 | 4/2005 | Brown-Skrobot et al. | |
| 2005/0106210 A1 | 5/2005 | Ding et al. | |
| 2005/0194391 A1 | 9/2005 | Domke et al. | |
| 2005/0214443 A1 | 9/2005 | Madsen | |
| 2005/0268573 A1 | 12/2005 | Yan | |
| 2005/0278012 A1 | 12/2005 | Vonderwalde | |
| 2006/0029722 A1 | 2/2006 | Larson et al. | |
| 2006/0043650 A1 | 3/2006 | Hossainy et al. | |
| 2006/0104858 A1 | 5/2006 | Potember et al. | |
| 2006/0147339 A1 | 7/2006 | Hunter et al. | |
| 2006/0153732 A1 | 7/2006 | Lee et al. | |
| 2007/0084144 A1 | 4/2007 | Labrecque et al. | |
| 2007/0280851 A1 | 12/2007 | Freeman et al. | |
| 2011/0209442 A1 | 9/2011 | Freeman et al. | |

FOREIGN PATENT DOCUMENTS

| | | |
|---|---|---|
| EP | 1 559 439 A1 | 8/2005 |
| EP | 1 019 107 B1 | 7/2006 |
| WO | WO 97/10011 A1 | 3/1997 |
| WO | WO 03/037390 A1 | 5/2003 |

OTHER PUBLICATIONS

U.S. Appl. No. 11/890,193, filed Aug. 2, 2007, McNiven et al.

"Changing Face of Sterilization", Editor D. Allen, Pharmaceutical & Medical Packaging News, Nov. 11, 1998, 4 pgs.

Agrawal et al., "The efficacy of acetone in the sterilisation of ophthalmic instruments", Indian J. of Ophthalmology 41, pp. 20-22 (1993).

Aseptic technique—Wikopedia, encyclopedia, downloaded, http://en.wikipedia.org/wiki/Sterile_technique, Aug. 7, 2007, 3 pgs.

Cleanroom Technology, "RABS: performance levels defined" (2005), downloaded, www.cleanroom-technology.co.uk/storyprint.asp?sc=35597, Aug. 7, 2007, 4 pgs.

Invitation to Pay Additional Fees for PCT/US2007/018231, filed Aug. 15, 2007, mailed Feb. 25, 2008, 5 pgs.

Dillow et al., "Bacterial Inactivation by Using Near-and Supercritical Carbon Dioxide", Proc. Natl. Acad. Sci. vol. 96, pp. 10344-10348 (1999).

Hart et al., "Effect of temperature on the sterilization of Isopropyl Alcohol by Liquid Propylene Oxide", J. of Appl. Microbiology 30, pp. 483-484 (1975).

Nahar et al., "Toxic effects of toluene on the growth of ac tivated sludge bacteria", World J. of Microbiology & Biotechnology 16, pp. 307-311 (2000).

P. Mosko et al., "Barrier Isolation Technology: A Labor-Efficient Alternative to Cleanrooms", Containment Technologies Group, downloaded, www.mic4.com/articles/labor-efficient-alternative.php, Aug. 7, 2007, 6 pgs.

Pharmaceutical Compounding, IJPC-Implementing USP Chapter <797>, downloaded, www.ijpc.com/products/ProductDescription.cfm?PID=2532, Aug. 7, 2007, 3 pgs.

Reitz, "Sterilization for beginners", Medical Design News, 2004, 3 pgs.

STERILIZATION METHODS FOR MEDICAL DEVICES

CROSS REFERENCE TO RELATED APPLICATIONS

This application is a division of U.S. patent application Ser. No. 11/893,230, filed on the 14 Aug. 2007, published as U.S. Patent Application Publication No. 2008-0044553 A1 on the 21 Feb. 2008, and issued as U.S. Pat. No. 8,747,738 B2 on the 10 Jun. 2014, and U.S. patent application Ser. No. 11/893,230 claims the benefit of U.S. Patent Application No. 60/838,030, filed on the 15 Aug. 2006. U.S. patent application Ser. No. 11/893,230 and U.S. Patent Application No. 60/838,030 are incorporated by reference herein in their entirety, including any drawings.

BACKGROUND OF THE INVENTION

Field of the Invention

This invention relates to methods of sterilization of medical devices, and particularly stents, a type of implantable medical device, and methods of preparing sterilized, packaged medical devices, including sterilized, packaged stents.

Background

This invention relates to methods of sterilization of articles, particularly medical devices, and more particularly, stents. In addition this invention relates to methods of preparing sterilized, packaged articles, and more particularly sterilized, packaged medical devices, including sterilized, packaged stents.

The term sterilization refers to the elimination of microorganisms such as fungi, bacteria, viruses and prions, or a reduction in the bioburden of an item where bioburden refers to the number of micro-organisms with which the item is contaminated. The degree of sterilization is typically measured by a sterility assurance level (SAL) which refers to the probability of a viable microorganism being present on a product unit after sterilization.

There are a number of sterilization procedures. The broad categories include heat, chemicals, irradiation, and filtration. An example of using heat to sterilize is autoclaving of medical instruments. Cooking or canning food is also another application of using heat for sterilization. A number of chemicals can be used for sterilization including ozone, chlorine bleach (sodium hypochlorite), formaldehyde/glutaraldehyde, ethylene oxide, hydrogen peroxide, and peracetic acid. Irradiation includes exposure to gamma rays, X rays, or ultraviolet rays or electron beam (Victoria Reitz, "Sterilization for Beginners," June 18, Medical Design Magazine). Filtration typically involves filtering through a 0.2 micron filter.

The choice of sterilization technique will depend upon the application, and the sterility level desired. The required SAL for a product is dependent on the intended use of the product. For medical devices in particular, the level of sterility for a Class I device as per United States Food and Drug Administration ("FDA") classifications, which presents a minimal risk of harm to the user and are simpler than Class II and Class III devices, will be different than the level required for a Class III device which "are usually those that support or sustain human life, are of substantial importance in preventing impairment of human health, or which present a potential, unreasonable risk of illness or injury." (FDA definition).

In addition the United States FDA regulates devices with most regulations for medical devices and radiation emitting products found Title 21 of the Code of Federal Regulations (CFR) parts 800-1299. Although the FDA does provide some guidance on sterility levels, more specific information can be found in guidance documents provided by the International Organization of Standards (ISO) documents which were developed in conjunction with Association for the Advancement of Medical Instrumentation (AAMI) (Reitz). SALs for various medical devices can be found in materials from the AAMI in Arlington, Va.

One type of medical device for which sterilization is required is a stent. A stent is a medical device belonging to the larger category of devices referred to as "endoprostheses." An "endoprosthesis" corresponds to an artificial device that is placed inside the body. Stents are shaped devices which function to hold open, and sometimes expand, a segment of a blood vessel or other anatomical lumen such as urinary tracts and bile ducts. A "lumen" refers to a cavity of a tubular organ such as a blood vessel. A stent is a Class III medical device per FDA medical device classifications. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter (for example the stent may be crimped onto the catheter, or onto a catheter balloon), inserting the end of the catheter through the skin into a bodily lumen, advancing the catheter in the bodily lumen to a desired treatment location, expanding the stent at the treatment location, and removing the catheter from the lumen.

Stents may also be medicated, that is manufactured to also deliver a drug, bioactive agent, or other active or bioactive agent to the patient. A medicated stent falls into the FDA definition (as per 21 CFR §3.2(e)) of a combination product due to the combination of a drug or biologic with a medical device. A medicated stent may be fabricated by coating the surface of the stent scaffolding with a polymeric carrier that includes an active or bioactive agent or drug, or in the alternative, if the stent contains a polymer, the polymer scaffolding may also serve as a carrier of an active agent or drug.

A number of techniques can be used to sterilize medical devices.

Many medical devices, such as but not limited to, stents, typically undergo terminal sterilization, that is sterilization occurs in the final packaged product, or for a stent, sterilization after fabrication, mounting on the delivery device, attachment to a delivery system and packaging. Thus, the sterilization operation may have a negative impact on the material comprising the stent or the material comprising the stent coating, and/or any drug, bioactive agents, or other additive in the coating on the stent.

SUMMARY OF THE INVENTION

The present invention relates to methods of sterilizing articles, more specifically medical devices including stents, and methods of preparing a sterile packaged article including sterile packaged medical devices including sterile packaged stents.

Some embodiments of the present invention include a method of sterilizing a stent, the method including: exposing the stent to a sterilizing chemical at ambient temperature; performing one or more processing operations on the exposed stent; and packaging the processed stent, wherein the sterility assurance level (SAL) of the packaged stent is less than a selected value due to the exposure to the sterilizing chemical.

Some embodiments of the present invention include a method of a method for preparing a sterilized packaged stent, the method including: exposing a stent comprising a polymer to radiation to sterilize the stent while the stent is in an uncrimped state; and packaging the stent.

Some embodiments of the present invention include a method of preparing a sterilized, packaged stent, the method including: exposing the stent to a fluid to a cleaning fluid in preparation for a coating operation; exposing the stent to a sterilizing chemical at ambient temperature; coating the stent; and heating the stent after coating, wherein the stent comprises a polymer.

Some embodiments of the present invention include a method of preparing a sterilized, packaged stent, the method including: exposing the stent to a cleaning fluid in preparation for a coating operation; coating the stent; and heating the stent after coating; mounting the stent onto a delivery device and attaching the mounted stent to a delivery system; packaging the stent and delivery system; and exposing the packaged stent and delivery system to radiation of not more than 15 KGy after packaging the stent; wherein the stent comprises a polymer.

DETAILED DESCRIPTION OF THE INVENTION

In the discussion that follows, to avoid the stilted language required to consistently indicate that the plural of various aspects of this invention is included with the singular, any reference to the singular implies the plural and visa-versa, unless expressly stated to be otherwise; for example, "a bioactive agent" or "the bioactive agent" will refer to a single bioactive agent or to a plurality of bioactive agents; "a polymer" or "the polymer" will refers to a single polymer or a plurality of polymers, "a sterilizing chemical" will refer to a single sterilizing chemical or a plurality of sterilizing chemicals, etc.

For the purposes of the present invention, the following terms and definitions apply:

The "glass transition temperature," $T_g$, is the temperature at which the amorphous domains of a polymer change from a brittle vitreous state to a solid deformable state. In other words, the $T_g$ corresponds to the temperature where the onset of segmental motion in the chains of the polymer occurs. When an amorphous or semi crystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. The measured $T_g$ of a given polymer can be dependent on the heating rate and can be influenced by the thermal history, and potentially pressure history, of the polymer, as well as potentially the pressure at which the measurement is made. Furthermore, the chemical structure of the polymer heavily influences the glass transition by affecting mobility.

The "melting temperature", $T_m$, of a polymer is the highest temperature at which a crystal lattice in the polymer is stable.

"Sterilize" or "sterilization"—the process by which the bioburden of an item is reduced to a particular sterility assurance level where the sterility assurance level required will depend upon the use of the article.

"Sterility Assurance Level" (SAL)—refers to the probability of a viable microorganism being present on a product unit (that is the product is not sterile) after the product has undergone sterilization procedure, or in other words, the probability that a particular unit is non-sterile after the product has undergone a sterilization procedure.

"Stent Preparation Step" or "Stent Preparation Operation"—a process or method in which a stent or other device is immersed in a solvent for a period of time to prepare the stent or device for coating and/or to potentially remove debris or other material from the stent or other medical device. This may also be referred to as exposing the stent to a fluid to a cleaning fluid in preparation for a coating operation.

"Patient"—an animal (an individual from a species included in the Kingdom animalia), including a human, in need of treatment for a disease or condition, or under medical care.

As used herein, an "implantable medical device" refers to any type of medical appliance that is totally or partly introduced, surgically or medically, into a patient's body or by medical intervention into a natural orifice, and which is intended to remain there after the procedure. The duration of implantation may be essentially permanent, as would be the case if the device is constructed of a biologically inert material, until it biodegrades and disappears or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, self-expandable stents, balloon-expandable stents, stent-grafts, grafts, artificial heart valves and cerebrospinal fluid shunts.

This invention relates to methods of sterilization of medical devices, and more particularly, stents, a type of implantable medical device. Various embodiments of this invention relate to methods of sterilization of implantable medical devices. As noted above, a stent is a type of "endoprosthesis" which corresponds to an artificial device that is placed inside the body. Stents are shaped devices which function to hold open, and sometimes expand, a segment of a blood vessel or other anatomical lumen such as urinary tracts and bile ducts, and are often used in the treatment of atherosclerotic stenosis in blood vessels. As noted above, the stent must be delivered, typically via a catheter, to the diseased site or lesion and then deployed.

Figure 1:
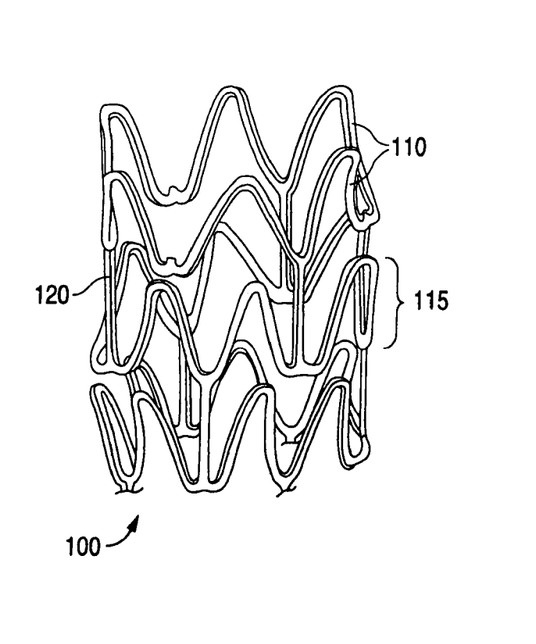
FIG. 1 depicts a stent.

In order to achieve the objectives of delivery to a site and then deployment, endoprotheses, including stents, may be radially expandable and may be adapted to be implanted in a bodily lumen. In particular, stents that are radially expandable have a structure designed such that it can be expanded in a body lumen. The structure of a stent is typically composed of, but not limited to, scaffolding that includes a pattern or network of interconnecting structural elements often referred to in the art as struts, or bar arms. An example of a stent is shown in FIG. 1. FIG. 1 depicts an exemplary stent 100 with struts 110 that form cylindrical rings 115 which are connected by linking struts 120. The scaffolding can be formed from wires, tubes, or sheets of material rolled into a cylindrical shape. The scaffolding is designed so that the stent may be radially compressed (for example to allow crimping to a smaller size to attach to a catheter or for other means of mounting on a delivery device) and radially expanded (to allow for deployment). A conventional stent is allowed to expand and contract through movement of individual structural elements of a pattern with respect to each other. The stent and stent pattern illustrated in FIG. 1 is an example of the type of stent structure or stent pattern that may be used in the present invention but the present invention is in no way limited to the stent structure or stent pattern that is illustrated in FIG. 1.

The stent must be able to satisfy a number of mechanical requirements due to the need to be delivered to the site of deployment, deployed at the chosen site, and then to perform the intended function in-vivo, that is holding open, and potentially expanding, the body lumen. First, the stent must possess adequate radial strength to withstand the structural loads, namely radial compressive forces, imposed on the stent as it supports the walls of a vessel. During preparation for delivery, for example by crimping or compressing around a balloon disposed on a catheter, and deployment the stent undergoes mechanical stresses and strains. Once deployed, the stent must adequately maintain its size and shape throughout its service life despite the various forces that may come to bear on it, including the cyclic loading induced by the beating heart.

As noted above, the stent may also be designed to deliver a drug or other bioactive agent, thus qualifying as a combination product as per FDA regulations. A medicated stent may be fabricated by coating the surface of the stent scaffolding with a polymeric carrier or another carrier material that includes an active, bioactive agent, drug, agent useful in diagnosis, or agent useful in visualization of the device, including proteins and other macromolecules. More generally, active agent will refer to an agent useful in the diagnosis, treatment, or prevention of a disease or condition, or the resulting symptoms thereof, or agent useful in the visualization of the device (collectively "active agent"). The coating material is applied as a solution, or dispersion, in a fluid, or solvent, where the fluid or solvent is substantially removed during processing. If the scaffold of the stent is a polymer, or includes a polymer, the scaffolding may also serve as a carrier of an active agent.

The scaffolding which forms the stent itself can be fabricated from metals, polymers, or a blend of polymers, or other materials. The stent must be biocompatible to reduce or prevent any adverse vascular responses, or other adverse responses. The underlying structure or substrate of a stent can be completely, or at least in part, made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

A polymer for use in fabricating an implantable medical device, such as a stent, or for use in a coating, can be biostable, bioabsorbable, biodegradable or bioerodable. Biostable refers to polymers that are not biodegradable. The terms biodegradable, bioabsorbable, and bioerodible are used interchangeably and refer to polymers that are capable of being completely degraded and/or eroded when exposed to bodily fluids such as blood, and can be gradually resorbed, absorbed, and/or eliminated by the body. The processes of breaking down and absorption of the polymer can be caused by, for example, hydrolysis and metabolic processes.

Representative examples of polymers that may be used to fabricate stents include, but are not limited to, poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoesters, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as, but not limited to, polyvinylidene chloride), polyacrylonitrile, polyvinyl ketones, polyvinyl aromatics (such as, but not limited to, polystyrene), polyvinyl esters (such as, but not limited to, polyvinyl acetate), acrylonitrile-styrene copolymers, ABS (acrylonitrile butadiene styrene) resins, polyamides (such as, but not limited to, Nylon 66 and polycaprolactam), polycarbonates, polyoxymethylenes, polyimides, polyethers, rayon, rayon-triacetate, cellulose acetate, cellulose butyrate, cellulose acetate butyrate, cellophane, cellulose nitrate, cellulose propionate, cellulose ethers, and carboxymethyl cellulose.

Additional representative examples of polymers that may be especially well suited for use in fabricating embodiments of implantable medical devices, including stents, disclosed herein include ethylene vinyl alcohol copolymer (commonly known by the generic name EVOH or by the trade name EVAL®), poly(butyl methacrylate), poly(vinylidene fluoride-co-hexafluoropropene) (e.g., SOLEF® 21508, available from Solvay Solexis PVDF, Thorofare, N.J.), polyvinylidene fluoride (otherwise known as KYNAR®, available from ATOFINA Chemicals, Philadelphia, Pa.), ethylene-vinyl acetate copolymers, poly(vinyl acetate), styrene-isobutylene-styrene triblock copolymers, and polyethylene glycol. Other polymers which may be especially well suited include, but are not limited to, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), and poly(glycolide-co-caprolactone).

A non-polymer substrate of the device may be made of a metallic material or an alloy such as, but not limited to, cobalt chromium alloy (ELGILOY®), stainless steel (316L), high nitrogen stainless steel, e.g., BIODUR® 108, cobalt chrome alloy L-605, "MP35N," "MP20N," ELASTINITE® (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 20% molybdenum. "MP20N" consists of 50% cobalt, 20% nickel, 20% chromium, and 10% molybdenum.

The typical stent manufacturing process starts with a tube for manufacturing the stent. The stent tube may be of any one of numerous shapes, but preferably, the tube may be cylindrical, or substantially cylindrical. The starting point of the manufacture may be with the tube itself, or the tube may be fabricated. A polymeric stent may be fabricated from a tube or a sheet that is rolled into a tubular shape, and bonded by any one of various techniques known in the art to form a tube. The tube or sheet may be formed by various processing methods known in the art, such as, but not limited to, extrusion or injection molding.

In a subsequent optional operation, the formed tube may be radially expanded to increase radial strength. During the radial expansion operation, the tube may optionally be heated to temperatures above $T_g$.

Typically, the next operation is the stent cutting operation. A stent pattern, such as but not limited to the one illustrated in FIG. 1, may be formed on a tube or sheet by laser machining or other methods known in the art. Representative examples of lasers that may be used include, but are not limited to, excimer, carbon dioxide, YAG (yttrium aluminum garnet), or a femtosecond laser such as, but not limited to, that developed by Lawrence Livermore National Laboratory. Other methods known in the art, such as but not limited to chemical etching, may be used to cut a stent pattern into the tube.

An alternative to the above operations of starting with a tube is to start with a sheet which may be cut with a stent pattern, and then rolled and sealed to form a tube by methods known in the art. Potentially the tube may be radially expanded, and potentially at a temperature above $T_g$. The stent pattern may be cut into the tube in much the same manner that a stent pattern may be cut in a tube as outlined above.

Optionally, the stent cutting operation is followed by "a stent preparation step," also referred to here as a "stent preparation operation." The stent preparation operation is a process in which the stent is immersed in a solvent, such as, but not limited to, 100% isopropyl alcohol, for a period of time to prepare the stent or device surface for coating. In addition to preparing the surface for coating, the stent preparation operation may also help in the removal of any debris from the stent. Thus, the "stent preparation operation" may be performed on the stent or device, even if the stent or device may not be coated. The stent preparation operation may be performed for a metal or a polymer stent.

An optional stent coating operation follows either the stent preparation operation (the immersion in solvent outlined above), or after the stent cutting operation, if no stent preparation operation is performed. During the coating operation a coating material may be applied to the stent via standard techniques known in the art, such as spray coating. The coating material may be a pure active agent, or the coating material may be, or include, active agent mixed, or dispersed, within a polymer carrier, or other type of carrier. The coating material is applied as a solution, or dispersion, in a fluid, or solvent, where the fluid or solvent is removed, or substantially removed, during processing. Multiple coating operations may be performed and more than one active agent, drug, and/or bioactive agent may be included in the stent coating. An optional subsequent operation may be to subject the stent to a heat treatment to remove residual fluid or solvent, and/or to cure, and/or potentially anneal, the polymer. The temperature can be somewhere in the range of about 40° C. to about 50° C., or even higher.

Typically, the next operation in the stent manufacturing process is to mount the stent onto the delivery device. The coated or uncoated stent may then be mounted on a delivery device, such as for example by crimping the stent on to a catheter balloon. Other methods of mounting the stent or device to a delivery device may be used. Optionally, a sheath may be placed over the crimped stent to retain the stent delivery device, to protect the stent, or both. The mounted stent or device may be attached to a delivery system, and then may be packaged.

Typically the stent is terminally sterilized, that is sterilization occurs once the stent has been manufactured, optionally coated, mounted on a delivery device, covered with a sheath if required, attached to a delivery system, and packaged. Conventional wisdom holds that terminal sterilization is preferred, and/or is required, to meet a particular sterility assurance level. For medical devices, a number of sterilization methods can be used such as autoclaving, treatment with ethylene oxide, and irradiation, including, but not limited to, both gamma irradiation and electron beam (e-beam) irradiation.

For surgical instruments an autoclave can be used. However, for more complex medical devices, the autoclave method may be undesirable because it requires exposure to moisture, as well as high temperatures in some cases, such as the boiling point of water, about 100° C. For a stent, high temperatures could damage or degrade the stent scaffolding, a stent coating, or an active agent.

The terminal sterilization of medical devices, including stents, may be performed by utilization of ethylene oxide or irradiation. Ethylene oxide ("EtO") sterilization is performed by spraying or immersing the device in liquid ethylene oxide, or exposing the device to gaseous ethylene oxide to obtain a desired bioburden level. Ethylene oxide is often used for plastics and hermetically sealed products. However, one disadvantage of ethylene oxide is the long turnaround time due to the need to wait for the dissipation of the ethylene oxide from the items sterilized (Pharmaceutical and Medical Packaging News Magazine, Daphne Allen, editor, "MEDICAL: The Changing Face of Sterilization, Advances in Existing Technologies and a Number of Emerging Methods are Helping Manufacturers Satisfy Rigorous Requirements," published in 1998). In addition, cycle times may be long to assure that the ethylene oxide reaches all the areas requiring sterilization, particularly for complex devices. To speed up this process, elevated temperatures may be used, but the elevated temperatures may have a negative impact on the product. Additionally, ethylene oxide is highly toxic.

Radiation sterilization is well known to those of ordinary skill the art. Medical devices composed in whole or in part of polymers can be sterilized by various kinds of radiation, including, but not limited to, electron beam (e-beam), gamma ray, ultraviolet, infra-red, ion beam, x-ray, and laser sterilization. A sterilization dose can be determined by selecting a dose that provides a required SAL. A sample can be exposed to the required dose in one or multiple passes. Irradiation refers to the exposure to radiation.

Gamma irradiation can penetrate materials of various densities and thus can be used for products in complex packages. Cobalt 60 can be used as a source of gamma rays. Electron beam (e-beam) irradiation involves the exposure to concentrated highly charged electrons generated by the acceleration and conversion of electricity. E-beam sterilization is generally used for high volume, low value products or low volume, high value products when used. One disadvantage of both gamma and e-beam radiation is that exposure may degrade materials via alteration of molecular bonds. In addition, for both types of irradiation, but particularly for gamma irradiation, the initial capital costs are high which may lead to out-sourcing and consequently longer operation times due to the need to transport to and from another facility.

Because implantable medical devices, including stents, typically undergo terminal sterilization, any active agents that are coated on the stent, or incorporated in the stent, are exposed to the sterilization medium and conditions. The exposure of the active agent to radiation or EtO may potentially have a negative impact on the active agent. Furthermore, the sterilization procedure may have an impact on the stent itself, particularly if the stent or device, and/or the stent or device coating, includes a polymer.

It is generally known that mechanical properties of a polymer may tend to change or age undesirably with time. For a polymer stent, such changes may potentially occur even though the product is sterilized using low doses of radiation (25 KGy) and at temperatures below ambient. A polymer stent may potentially be particularly sensitive to degradation by standard radiation doses. Currently AAMI standards require a minimum dose level of approximately 10.4 KGy to achieve an SAL of $10^{-6}$. Such exposure may potentially result in undesirable deterioration of the mechanical properties of a stent. Aging may potentially be reduced or prevented by storing a stent at cold storage conditions.

The terminal sterilization may be performed by utilization of EtO or electron beam irradiation. Both procedures may have a negative impact on the mechanical properties of the material forming the stent, particularly if the stent contains a polymer, and/or if there is any stent coating. In addition, either sterilization procedure may potentially have a negative impact on any active agent that may be contained in the coating and/or is incorporated in the stent. As noted above the stent undergoes a number of mechanical stresses and strains during the preparation for packaging, the delivery of the stent to the site of deployment, as well as the expansion or deployment of the stent, in addition to the mechanical stresses that it undergoes during in-vivo use. Thus, any degradation or decrease in the mechanical properties is undesirable.

Various embodiments of sterilization methods are described herein. The sterilization methods may potentially lead to improved mechanical properties of the implantable medical device (including a stent), longer shelf life of the implantable medical device (including a stent), and more flexibility in storage conditions for the devices (including a stent). Additionally such sterilization methods may allow the use of a wider variety of bioactive agents, active agents, diagnostic agents, and/or drugs that may be used in the manufacture of a medicated device (including a stent) since some agents are sensitive to current sterilization methods. Furthermore, the sterilization methods may allow for other materials to be used in the manufacture of implantable medical devices, in particular those materials that have not been used due to concern that the properties of the material will be negatively impacted by sterilization with either EtO or radiation. All embodiments of the present invention may not necessarily exhibit or possess all of the potential advantages aforementioned.

In addition to alternative methods for the sterilization of a medical device, particularly an implantable medical device, including a stent, a number of methods for the preparation of sterilized packaged medical devices, including sterilized, packaged stents, are also described herein.

In certain embodiments, a stent may be sterilized through application of a sterilizing chemical. The chemical sterilization may be performed as an alternative to radiation sterilization, or EtO sterilization, both of which can involve exposing the device to temperature above ambient that can be harmful to the stent.

Embodiments of chemical sterilization are a viable alternative to either EtO sterilization or radiation sterilization due to the nature of the stent manufacturing process. More particularly, it is believed that the bioburden on the stent during processing is limited to the surface of the stent. The bioburden in a region beneath a surface region of the stent is likely to be eliminated during extrusion and expansion of the product since the polymer is exposed to high temperatures during these operations. When a polymer is used for the scaffolding of a stent or device, a typical manufacturing process requires that the tubing is extruded, expanded, and packaged in a controlled environment. Therefore, due to the nature of the processing, it is believed that the tubing probably exhibits a very low baseline bioburden.

In certain embodiments, chemical sterilization refers to sterilization through exposure of an article, such as a medical device or stent, to a chemical at ambient temperature. Ambient or room temperature refers to a temperature in the range of about 15° C. to about 30° C., such as for example, but not limited to 20° C., 22° C., 25° C. or 27° C., or more narrowly in the range of 20° C. to 27° C., or 20° C. to 25° C., or 22° C. to 27° C.

In some embodiments, the chemical sterilization may be performed at a temperature slightly higher than ambient. In particular, for a metal stent, the chemical sterilization may occur at a temperature higher than ambient temperature. The upper limitation on the temperature may be set by the boiling point of the sterilizing chemical. In some embodiments, a metal stent may be sterilized by exposure to a sterilizing chemical at a temperature at above 30° C. or above 40° C., or even 50° C. or higher. In still other embodiments, a stent which includes a polymer as part of the stent body and/or as part of a coating, may be subjected to chemical sterilization wherein the temperature is slightly above ambient, such as, but not limited to, about 30° C. to about 35° C., about 35° C. to about to 37° C., or 35° C. to 40° C. wherein about, as used in this sentence, means within 2 to 3° C.

The sterilizing chemical may be any substance, whether gas, liquid, fluid, or solid, that reduces the bioburden to a desired level on the device upon exposure to the chemical for a sufficient time period. For example, the sterilizing chemical may include toluene, formaldehyde, acetone, isopropyl alcohol, or combinations thereof.

For example, combinations of toluene in any of the other three aforementioned chemicals (formaldehyde, acetone, isopropyl alcohol) may be 5%, 10%, 15%, 20%, 25%, 30%, 35%, 40%, 45%, 50%, 55%, 60%, 65%, 70%, 75%, 80%, 85%, 90%, 95% or any of the ranges between those stated as well as less than 5% and greater than 95%. For example, combinations of acetone in any of the other three aforementioned chemicals (toluene, formaldehyde, isopropyl alcohol) may be 5%, 10%, 15%, 20%, 25%, 30%, 35%, 40%, 45%, 50%, 55%, 60%, 65%, 70%, 75%, 80%, 85%, 90%, 95% or any of the ranges between those stated as well as less than 5% and greater than 95%. For example, combinations formaldehyde in any of the other three aforementioned chemicals (toluene, acetone, isopropyl alcohol) may be 5%, 10%, 15%, 20%, 25%, 30%, 35%, 40%, 45%, 50%, 55%, 60%, 65%, 70%, 75%, 80%, 85%, 90%, 95% or any of the ranges between those stated as well as less than 5% and greater than 95%. For example, combinations isopropyl alcohol in any of the other three aforementioned chemicals (toluene, formaldehyde, acetone) may be 5%, 10%, 15%, 20%, 25%, 30%, 35%, 40%, 45%, 50%, 55%, 60%, 65%, 70%, 75%, 80%, 85%, 90%, 95% or any of the ranges between those stated as well as less than 5% and greater than 95%. The combinations above are expressed as volume % of each solvent prior to mixing the solvents together. For example a mixture of 200 ml of acetone with 200 ml of toluene would be referred to as 50% toluene and 50% acetone even if the final mixture has a volume of less than or more than 400 ml.

For combinations of three or four of the sterilizing chemicals, each chemical may range from less than 5%, 5%, 10%, 15%, 20%, 25%, 30%, 35%, 40%, 45%, 50%, 55%, 60%, 65%, 70%, 75%, 80%, 85%, 90%, 95%, or greater than 95% as well as ranges between those stated, provided that the sum of the all three or the sum of all four is 100%. The sterilizing chemical may be of a pharmaceutical grade or any other grade appropriate for the process. The sterilizing chemical may be free of, or substantially free of, particulates.

In some embodiments, the presence of a significant fraction of water may be detrimental to the stent. In particular, if the stent includes a biodegradable polymer, particularly one that hydrolyzes, exposure to water may damage or degrade the polymer. In other embodiments, the stent may be metallic and/or the stent may include polymer or other materials that are not susceptible to degradation by water, and therefore, the presence of water may not have any impact, or only an insubstantial impact, upon the stent. Therefore, in some embodiments, some water may be present during the chemical sterilization process.

With respect to the sterilizing chemical (which may be a combination of chemicals), water may be present at levels from less than 5%, 5%, 10%, 15%, 20%, 25%, 30%, 35%, 40%, 45%, 50%, 55%, 60%, 65%, 70%, 75%, 80%, 85%, 90%, 95%, to greater than 95%. The combinations above are expressed as volume % of each solvent prior to mixing the solvents together.

In some embodiments, a medical device can be exposed to a sterilizing chemical under conditions of ambient humidity. Ambient humidity can refer to a relative humidity between 0 and 100%, or between about 10% and about 75%, or more narrowly, between about 15% to about 65%. In other embodiments, chemical sterilization can be performed under conditions of controlled humidity. In such embodiments, the relative humidity can be controlled to be less than about 60%, less than about 50%, less than about 40%, less than about 30%, less than about 20%, less than about 15%, less than about 10%, or less than about 5%.

In some embodiments, an article, such as a medical device, may be sprayed with or immersed within the sterilizing chemical which is in a liquid state to achieve chemical sterilization. In other embodiments, the medical device may be exposed to a vapor of the sterilizing chemical. In other embodiments, the sterilizing chemical may be applied on the surface of the medical device or stent with an article, such as a sponge, cloth, paper towel, paper tissue or other article that will absorb liquid that has been immersed in the sterilizing chemical which is in a liquid state. Additional embodiments may include any other methods of exposing the medical device, including a stent, to a fluid, including a sterilizing chemical. In further embodiments, the medical device can be exposed two or more times to a sterilizing chemical. In such embodiments, the device may be exposed using any combination of the methods disclosed.

The time frame for the exposure may be determined by the time required to obtain a desired SAL. It is believed that the time frame for the exposure may depend upon such factors as the nature of the chemical sterilizing agent, the manner of exposure, and the nature of the article to be sterilized, as well as the use of standard techniques for measuring sterility, or validating that a process produces a given SAL.

In some embodiments, the chemical sterilization may be performed aseptically. A process is performed aseptically if it is performed under sterile conditions. Aseptic generally means sterile or free from bacterial contamination. For example, a stent can be sterilized in a sterile, isolated chamber such as a commonly available sprayer hood provided that it has been configured to be a sterile isolation barrier. In such embodiments, the sprayer hood may be validated as a sterile isolation barrier. In such embodiments, one or more subsequent stent processing operations may be performed in an aseptic environment. In some embodiments, the stent, or medical device, can be chemically sterilized in an environment which is not aseptic, and one or more subsequent processing operations may be performed in an aseptic environment.

An exemplary isolation barrier is an absolute isolation barrier available from Flanders/CSC. In some embodiments, an isolation barrier may be specifically designed with the capability for sterilizing the entire isolation barrier, and therefore, it is designed specifically for use in aseptic processing. In other embodiments, an isolation barrier may be designed for use with toxic active agents, and may be configured in a manner and/or used with procedures such that it is may be used for aseptic processing.

In some embodiments, the operations after, and optionally including, the chemical sterilization operation may be carried out aseptically, but without the use of an isolation barrier. Although an isolation barrier may be used in aseptic processing, it is not required. In some embodiments, a class 100 laminar flow hood may be used for aseptic processing.

Conventional equipment that is known in the art, such as, but not limited to, pumps, vacuum pumps, heating or cooling devices, filters or other ventilation equipment may also be required or desirable. In addition, spray nozzles, with or without air or other gas for atomization, may be utilized, and are well known in the art. For applications involving flammable solvents, the equipment used may be explosion proof.

In some embodiments, all stent processing operations subsequent to, and optionally including, the chemical sterilization operation, may be performed aseptically. In some embodiments, stents may be processed in an aseptic environment. In such embodiments, the sterilized stent may be coated, and mounted on a delivery system in the aseptic environment. In some embodiments, the uncoated stent may be attached to the delivery system as an aseptically prepared unit. In such embodiments, if the stent, or other accessories and/or tools, are to be transported from one sterile area to another sterile area, the stent, or other accessories, may be double or triple bagged to reduce, or prevent, exposure to a non-sterile environment. The multiple coverings allow the item may be moved from one sterile area to another because the outer layer may be removed and the inner material may be passed to an uncontaminated area or person.

In further embodiments, the chemical sterilization may occur at one or more points in the stent manufacturing process prior to the final operation of packaging. In some embodiments, the chemical sterilization may be performed on a stent after laser cutting, but prior to spray coating. In some embodiments, the chemical sterilization may be performed prior to the stent preparation operation. In other embodiments, the chemical sterilization may be performed after the stent preparation operation, but prior to the coating operation. In other embodiments, the chemical sterilization may be performed as an alternative to the stent preparation operation.

In other embodiments, the stent preparation operation may be sufficient to sterilize the device. In some embodiments, the stent may undergo one or more stent preparation operations. In such embodiments, the preparation of a sterilized packaged stent may be obtained by executing all operations subsequent to the first, or only, stent preparation operation in an aseptic manner, such as, but not limited to, in an isolation barrier. In some embodiments, the stent preparation operation may also be performed aseptically.

In other embodiments, both the stent preparation operation and the chemical sterilization operation may both be required to achieve the required sterility assurance level. In some embodiments the stent preparation operation may be performed first, while in other embodiments the chemical sterilization operation may be performed first. In some embodiments more than one chemical sterilization operation and/or more than one stent preparation operation may be performed and the order in which the operations are performed may vary. Aseptic processing may be used to ensure the sterility of the final packaged product.

In some embodiments there may be multiple chemical sterilization operations and/or multiple stent preparation operations. In some embodiments, the sterility of the final packaged product is assured by use of aseptic processing after a chemical sterilization operation. In further embodiments, the sterility of the final packaged stent is ensured by use of aseptic processing beginning after a stent preparation operation. In some embodiments, aseptic processing is initiated with a chemical sterilization operation or a stent preparation operation earlier in the process.

In some embodiments, the chemical sterilization operation may occur before the coating operation, either before or after the stent preparation operation. In other embodiments the chemical sterilization operation may occur after the coating operation. In other embodiments, the chemical sterilization operation may occur after the coating operation and prior to the optional post-coating heat treatment. In other embodiments, the chemical sterilization operation may be performed after the post coating heat treatment.

In certain embodiments, processing a stent may include the removal of undesirable or objectionable residue subsequent to the chemical sterilization operation, and/or the stent preparation operation. In some embodiments, the removal operation may include processing of the device with fluids that can remove all or some of such residue ("removal fluids"). Such objectionable or undesirable residue may include residual sterilizing chemicals, substances in the sterilizing fluid, or residual solvent from the stent preparation operation. Such removal solvents may be miscible with the sterilizing chemical and have a higher volatility. Acetone and isopropanol are exemplary removal fluids. Objectionable residue can be defined as residual solvent or other substances present in a stent at a level that can be harmful to a patient. In some cases, levels of acceptable solvent or other residue may be set by various regulatory agencies. In some embodiments, the stent may be rinsed with isopropanol or acetone even if the sterilizing fluid includes isopropanol and/or acetone. In such embodiments, the final rinse with a removal fluid is used to remove other substances, such as contaminants in the sterilizing fluid, and/or other substances which may provoke a biological or pyrogenic response.

The sterility of the final packaged medical device, including a packaged stent, may be obtained by repeated chemical sterilization operations, stent preparation operations, aseptic processing, and/or use of other sterilization procedures known in the art, or any combination of the aforementioned procedures.

In an exemplary embodiment, the chemical sterilization operation may be performed aseptically after a stent preparation operation, the stent may be coated, and a second chemical sterilization operation may be performed aseptically on the coated stent. In such exemplary embodiment, all subsequent operations performed on the stent, including, but not limited to, crimping the stent onto a delivery device, attaching the mounted stent/device assembly to a delivery system, and packaging the combination of stent and delivery system, may be performed aseptically.

In those embodiments in which the stent is processed aseptically, all of the accessories, equipment and tools needed for such operations may be pre-sterilized prior to the operations involving the stent, and prior to introduction into the isolation barrier or other area of aseptic processing. The sterilization of the tools, equipment or accessories, such as but not limited to, the delivery device, the delivery system, the sheath, and the packaging materials, may be executed by any means known in the art that will not have a deleterious effect on the tools, equipment or accessories. These methods include, but are not limited to, exposure to ethylene oxide, exposure to radiation including both gamma radiation and electron beam radiation, and exposure to steam or hydrogen peroxide. Other methods known in the art may be used for sterilization of the accessories, tools, and equipment required or desirable for the subsequent stent processing operations.

In some embodiments, even though a stent preparation operation and/or a chemical sterilization operation may be performed, a final terminal sterilization operation may be performed after packaging. In such embodiments, the terminal sterilization operation can include irradiation that utilizes a lower level of radiation than that would be required to sterilize without the prior chemical sterilization. Although the following embodiments may focus on e-beam sterilization, the embodiments will extend to other forms of irradiation for sterilization. For example, the dose for e-beam sterilization can be about 15 KGy or less, and preferably 5-15 KGy. Therefore, the lower level of terminal sterilization with the e-beam is possible because sterility is not dependent upon only the exposure to the e-beam radiation. Thus, in some embodiments, the use of the chemical sterilization operation and/or stent preparation operation, along with aseptic processing for subsequent operations, may be followed by a terminal sterilization step utilizing a lower level of radiation exposure.

In some embodiments, the lower level terminal sterilization may occur at a temperature below ambient temperature, such as less than 10° C., 0° C., −15° C., −25° C., −40° C., −70° C., −100° C., −150° C., −200° C., −240° C., or less than −270° C. Such embodiments may allow for more flexibility in manufacturing the implantable medical device, while obtaining potential benefits from reduced radiation exposure.

Some embodiments of the present invention relate to methods of preparing a sterilized packaged stent, in which the stent is subjected to the stent preparation step, the coating operation, and the post-coating heating operation. In some embodiments the combination of the stent preparation step, the coating operation, and the post-coating heating operation may yield a stent with an acceptable SAL. Therefore, all subsequent processing operations on the medical device, including a stent, may be executed in an aseptic manner, and/or other sterile manners known in the art, to produce a sterile, packaged stent.

Some embodiments of the present invention also relate to alternative methods of sterilization in which radiation may be used for sterilization. As indicated above, a polymer stent and delivery system are typically sterilized by electron beam radiation, or other radiation, after assembly and packaging. It is generally known that mechanical properties of a polymer may tend to change or age undesirably with time. For a polymer stent, such changes may potentially occur even though the product is sterilized using low doses of radiation (25 KGy) and at temperatures below ambient. Aging may be reduced or prevented by storing a stent at cold storage conditions. It is believed that aging of a polymer stent may be facilitated by the electron beam exposure of the stent while it is in a stressed state, i.e., crimped on the delivery system. Thus, the invention further provides for a method of sterilizing an implantable medical device, such as, but not limited to, a stent, with radiation when the device is in an unstressed state or undeformed state.

It is believed that if the sterilization by radiation occurs while the device is in an undeformed, or "as fabricated," state, the rate of aging or degradation of the polymer will be reduced, thus producing a stent, which may be more robust and may have a longer shelf life. For the purposes of the present invention, "deformed state" means that the stent is crimped, or otherwise mounted onto a delivery device.

Although the following embodiments may focus on e-beam sterilization, the various embodiments of the present invention will extend to other forms of irradiation for sterilization as well. As outlined above radiation sterilization is well known to those of ordinary skill the art. The various kinds of radiation that can be used for sterilization, include, but are not limited to, electron beam (e-beam), gamma ray, ultraviolet, infra-red, ion beam, x-ray, and laser sterilization.

In some embodiments, the implantable medical device may be sterilized by exposure to radiation, such as but not limited to, electron beam radiation, before it is crimped and mounted onto a delivery device, attached to a delivery system, and packaged. In such an embodiment the electron beam sterilization may occur after the stent has been coated and subjected to the post-coating heat treatment (at about 40° C. to 50° C. as outlined above). In other embodiments, the electron beam irradiation occurs prior to the post-coating heat treatment. In still other embodiments, the stent is sterilized by exposure to radiation prior to coating. In such embodiments where sterilization occurs prior to coating, the coating as well as any potential active agent in the coating, is not exposed to radiation. In some embodiments, all of the operations subsequent to the sterilization by exposure to radiation, including the final packaging operation, may be carried out aseptically.

In such embodiments in which the stent is sterilized in the undeformed state, the sterilization may occur at a temperature below ambient temperature, such as less than 10° C., 0° C., −15° C., −25° C., −40° C., −70° C., −100° C., −150° C., −200° C., −240° C., or less than −270° C.

In such embodiments where the stent is sterilized in the undeformed state, the catheter delivery system, sheath, and packaging material may be pre-sterilized by any technique known in the art, such as but not limited to, irradiation with electron beam radiation or gamma radiation, and/or sterilization with ethylene oxide. The stent may be crimped, inserted in to the sheath, attached to the delivery system, and then packaged. In some embodiments, all of the preceding operations are executed aseptically, and potentially in an isolation barrier. Since the performance of the catheter delivery system, sheath, and packaging material may be less sensitive to electron beam radiation or ethylene oxide than a stent, these other sterilization techniques may be used in the separate sterilization prior to aseptic assembly.

In other embodiments, the stent may be sterilized by exposure to radiation, such as by, but not limited to, electron beam radiation, while the stent is in an undeformed state, either before or after it is optionally coated. The sterility of the final packaged medical device, including a packaged stent, may be obtained by utilization of chemical sterilization operations, aseptic processing, and/or utilization of other sterilization procedures known in the art, or any combination of the aforementioned methods.

In an exemplary embodiment, aseptic processing may be used for all stent processing operations subsequent to the stent's exposure to radiation, up to and including the final packaging operation. Another exemplary embodiment may involve using radiation to sterilize the stent prior to coating, coating the stent, performing a chemical sterilization operation on the coated stent aseptically, and subsequently aseptically executing the operations of crimping the device onto a delivery device, attaching the crimped device/delivery device assembly to a delivery system, and packaging the stent/delivery device/delivery system.

In some embodiments of the current invention, terminal sterilization with radiation is used, but the exposure to radiation is at a lower level. Thus, all of the prior operations steps are carried out in such a manner as to reduce or maintain a low bioburden on the product in each step allowing a lower level of radiation to be used for the terminal sterilization. Therefore, in some embodiments a sterilized packaged stent is prepared by executing all of the processing operations in such a manner as to reduce or maintain a low bioburden in the product, thus allowing the final terminal sterilization to be executed with a lower total exposure to radiation. The lower level of sterilization may be 5 to 15 KGy, and not more than 15 KGy.

Embodiments of the sterilization of the present invention can provide an SAL less than $1 \times 10^{-6}$. In other embodiments, the sterilization can yield an SAL greater than $1 \times 10^{-6}$, or more narrowly, $1 \times 10^{-5}$ or $1 \times 10^{-4}$. In some embodiments, the sterilization can yield an SAL of $1 \times 10^{-3}$ which may be sufficient for some medical devices and under some circumstances.

In some embodiments, sterilization can yield a final packaged product with a 3, 4, 5 or 6, or greater, log reduction in bioburden. In some embodiments, after the last chemical sterilization step or stent preparation step, there may be a 3, 4, 5 or 6, or greater, log reduction in bioburden.

In a preferred embodiment of the present invention, a stent, may be manufactured from a tube comprising a biodegradable polymer. In some embodiments, the tube may be radially expanded at a temperature above the $T_g$ prior to laser cutting the stent pattern in the tube to form the stent. The device may subsequently be subjected to the stent preparation operation in which it is immersed in a solvent, preferably isopropyl alcohol. The removal from the isopropyl alcohol may occur in an isolation barrier. The stent may then be chemically sterilized utilizing a different solvent, preferably acetone, by spraying the solvent onto the stent or immersing the stent in the solvent. After the chemical sterilization with acetone, the stent may be optionally further processed to remove the residual solvent, acetone. The stent is then coated, crimped onto a delivery device, attached to a delivery system. The coating, crimping and attachment to a delivery system may occur within the isolation barrier which allows for aseptic processing. Subsequently, the final delivery system and stent are packaged in a laminar flow hood which also allows for aseptic processing. Any materials needed such as the delivery device, the sheath, the delivery system, and packaging materials, as well as tools and equipment that may be needed to execute the above steps can be pre-sterilized prior to introduction into the isolation barrier or the laminar flow hood.

In another preferred embodiment of the present invention, the stent comprising a biodegradable or bioabsorbable polymer, may be sterilized with electron beam irradiation prior to crimping the stent onto a delivery device. Thus, in this manner the stent is exposed to radiation while in an undeformed state. Subsequently, the stent may be optionally coated (if not already coated), crimped onto a catheter, attached to a delivery system, and packaged all in an isolation barrier which allows for an aseptic environment. As in the embodiment above, any materials needed such as the delivery device, the sheath, the delivery system, and packaging materials, as well as tools and equipment that may be needed to execute the above steps can be pre-sterilized prior to introduction into the isolation barrier.

Terms such a "element", "member", "device", "section", "portion", "step", "means" and words of similar import when used herein shall not be construed as invoking the provisions of 35 U.S.C. §112(6) unless the following claims expressly use the term "means" followed by a particular function without specific structure or the term "step" followed by a particular function without specific action.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for preparing a sterilized packaged stent, the method comprising:
    exposing a stent comprising a polymer to radiation to sterilize the stent while the stent is in an uncrimped state;
    after exposing the stent to radiation to sterilize the stent, coating the stent aseptically; and
    packaging the coated stent to form the sterilized packaged stent.

2. The method of claim 1, wherein the stent is exposed to radiation to sterilize the stent prior to mounting the stent on a delivery device.

3. The method of claim 1, further comprising mounting the coated stent onto a delivery device.

4. The method of claim 1, further comprising performing one or more additional stent processing operations, wherein all of the one or more stent processing operations subsequent to the exposure of the stent to radiation to sterilize the stent are performed aseptically.

5. The method of claim 1, wherein the sterilization is electron beam sterilization.

6. The method of claim 1, wherein the polymer is selected from the group consisting of poly(N-acetylglucosamine) (Chitin), Chitosan, poly(3-hydroxyvalerate), poly(lactide-co-glycolide), poly(-hydroxybutyrate), poly(-hydroxybutyrate), poly(3-hydroxybutyrate-co-3-hydroxyvalerate), polyorthoesters, polyanhydrides, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amides, poly(glycolic acid-co-trimethylene carbonate), co-poly(ether-esters) (e.g. PEO/PLA), polyphosphazenes, fibrin, fibrinogen, cellulose, starch, collagen, hyaluronic acid, polyurethanes, silicones, polyesters, polyolefins, polyisobutylene and ethylene-alphaolefin copolymers, acrylic polymers and copolymers, vinyl halide polymers and copolymers, polyvinyl chloride, polyvinyl ethers, polyvinyl methyl ether, polyvinylidene halides, polyvinylidene chloride, polyacrylonitrile, polyvinyl ketones, polyvinyl aromatics, polystyrene, polyvinyl esters, acrylonitrile-styrene copolymers, acrylonitrile butadiene styrene resins, polyamides, Nylon 66, polycaprolactam, polycarbonates, polyoxymethylenes, polyimides, polyethers, rayon, rayon-triacetate, cellulose acetate, cellulose butyrate, cellulose acetate butyrate, cellophane, cellulose nitrate, cellulose propionate, cellulose ethers, carboxymethyl cellulose, ethylene vinyl alcohol copolymer, poly(butyl methacrylate), poly(vinylidene fluoride-co-hexafluoropropene), polyvinylidene fluoride, ethylene-vinyl acetate copolymers, poly(vinyl acetate), styrene-isobutylene-styrene triblock copolymers, polyethylene glycol, and combinations thereof.

7. The method of claim 1, wherein the stent further comprises a drug.

8. The method of claim 1, wherein the stent further comprises a bioactive agent.

9. The method of claim 1, wherein the stent further comprises a protein.

10. The method of claim 1, wherein the stent further comprises a macromolecule.

* * * * *